(12) United States Patent
Grimme et al.

(10) Patent No.: US 8,702,793 B2
(45) Date of Patent: Apr. 22, 2014

(54) IMPLANTABLE ONE-PIECE HEART PROSTHESIS

(75) Inventors: Marc Grimme, Paris (FR); Jean-Elie Gourgues, Versailles (FR); Alain Carpentier, Paris (FR); Claude Wartelle, Gouvieux (FR)

(73) Assignee: Carmat, Velizy Villacoublay (FR)

( * ) Notice: Subject to any disclaimer, the term of this patent is extended or adjusted under 35 U.S.C. 154(b) by 617 days.

(21) Appl. No.: 12/812,588

(22) PCT Filed: Jan. 7, 2009

(86) PCT No.: PCT/FR2009/000008
§ 371 (c)(1),
(2), (4) Date: Sep. 27, 2010

(87) PCT Pub. No.: WO2009/112662
PCT Pub. Date: Sep. 17, 2009

(65) Prior Publication Data
US 2012/0089226 A1    Apr. 12, 2012

(30) Foreign Application Priority Data
Jan. 14, 2008  (FR) ..................... 08 00184

(51) Int. Cl.
*A61M 1/10* (2006.01)

(52) U.S. Cl.
USPC .................. 623/3.21; 623/3.1; 623/3.16

(58) Field of Classification Search
USPC ......................... 623/3.21, 3.1, 3.16
See application file for complete search history.

(56) References Cited

U.S. PATENT DOCUMENTS

| 4,687,424 A | 8/1987 | Heimes |
| 5,135,539 A | 8/1992 | Carpentier |

FOREIGN PATENT DOCUMENTS

| FR | 2 585 250 | 1/1987 |
| WO | 01/91828 | 12/2001 |

OTHER PUBLICATIONS

International Search Report dated Sep. 17, 2009.

*Primary Examiner* — Thomas J Sweet
*Assistant Examiner* — Matthew Schall
(74) *Attorney, Agent, or Firm* — Dickinson Wright PLLC

(57) ABSTRACT

Disclosed is an implantable one-piece heart prosthesis having a driving artificial ventricle and a driven artificial ventricle. A main actuator is configured to transmit to the driving artificial ventricle diastolic and systolic flow rates having desired respective values for the driving artificial ventricle. An auxiliary actuator is configured to transmit to the driven artificial ventricle correction systolic and diastolic flow rates that correct the systolic and diastolic flow rates transmitted by the main actuator to the driven artificial ventricle.

7 Claims, 6 Drawing Sheets

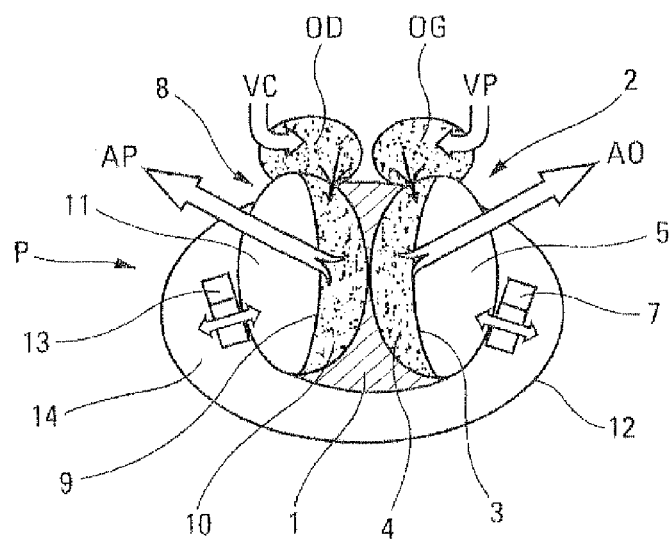
Fig. 1 PRIOR ART
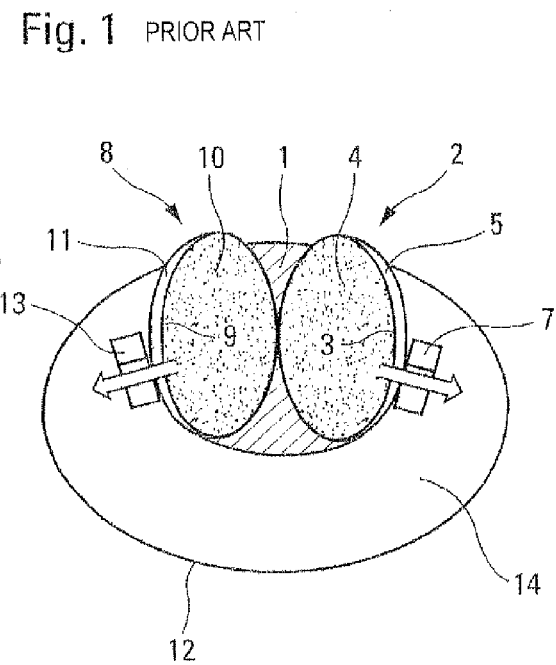
Fig. 2 PRIOR ART
Fig. 3 PRIOR ART

IMPLANTABLE ONE-PIECE HEART PROSTHESIS

FIELD OF THE INVENTION

This invention relates to an implantable one-piece heart prosthesis.

BACKGROUND OF THE INVENTION

From document U.S. Pat. No. 5,135,539, a heart prosthesis being implantable in the pericardial cavity of a patient is known, said prosthesis being capable of replacing the natural left and right ventricles of said patient after ablation thereof and comprising:
- a stiff body in which artificial left and right ventricles are arranged, each of these artificial ventricles comprising a soft pulsatile membrane:
  - which is capable of beating under the action of a hydraulic fluid, and
  - which is provided within a cavity sealingly partitioned by said membrane into two chambers, one of which is intended for blood flow and the other of which is intended for said hydraulic fluid, the blood chamber of the artificial left ventricle being intended to be connected to the natural left atrium and to the aorta, whereas the blood chamber of the artificial right ventricle is intended to be connected to the natural right atrium and to the pulmonary artery;
- two hydraulic actuators connected to the hydraulic fluid chambers of said cavities within said stiff body, for alternately injecting therein and expulsing therefrom hydraulic fluid and providing desired values of diastolic and systolic flow rates; and
- a soft bag widely and sealingly surrounding at least one portion of said stiff body while enclosing said hydraulic actuators, said soft bag serving both as a hydraulic fluid reservoir for said hydraulic actuators and as a compliance chamber.

In this known heart prosthesis, each actuator is associated with a ventricle and, in order to comply with physiology, both actuators can operate independently from each other and particularly in a synchronised way, that is both ventricles can be respectively and simultaneously either in diastole or in systole. In this case, the result is that said soft bag undergoes large displacements, since the whole fluid required for animating right and left pulsatile membranes is alternately injected, and then drawn into said soft bag. If the capacity of each ventricle is of about 75 cm$^3$, the volume variations of the bag may reach 150 cm$^3$. Such high amplitude beats of the bag, on the one hand, may raise issues of housing said prosthesis within the pericardial cavity and, on the other hand, cause an inflammation of the surrounding tissue, with the risk for a thick fibrous capsule to occur, capable of hindering the beats of the bag and altering the operation of the prosthesis.

Besides, such a synchronised operation requires that both actuators are capable of the same performance, which is of a high power cost.

In order to overcome these drawbacks, it could be possible, as suggested by document WO-0,191,828, to remove one of said actuators and operate the ventricles in phase opposition, one of said ventricles being in diastole whereas the other is in systole. Thus, the hydraulic fluid is transferred from a ventricle into the other with much reduced beats of the bag. In addition, such a heart prosthesis is advantageous in terms of space and power consumption, since it only comprises one actuator. However, it has the drawback of controlling the intake duration of one of the ventricles based on the ejection of the other, such that the diastole durations are necessarily equal to the systole durations, which does not enable physiology to be complied with. In addition, such a heart prosthesis with one single actuator has the risk, in operation, of either drawing the atria and failing to fill the ventricles, or performing too slow ejection and not maintaining a proper pressure.

SUMMARY OF THE INVENTION

This invention aims at overcoming these drawbacks by improving the heart prosthesis with two actuators described above.

For this purpose, according to the invention, such a heart prosthesis with two actuators is remarkable in that:
- one of said actuators is a main one and is provided between the hydraulic fluid chambers of both artificial ventricles, one of which is driving and the other is driven;
- the other of said actuators is a auxiliary one and is provided between the hydraulic fluid chamber of said driven artificial ventricle and said reservoir of hydraulic fluid made up by said soft bag;
- the main actuator:
  - transmits to said driving artificial ventricle diastolic and systolic flow rates having desired respective values for this driving artificial ventricle, and
  - transmits to said driven artificial ventricle:
    - a systolic flow rate opposite to said diastolic flow rate of a desired value for said driving artificial ventricle, and
    - a diastolic flow rate opposite to said systolic flow rate of a desired value for said driving artificial ventricle; and
  - the auxiliary actuator transmits to said driven artificial ventricle correction systolic and diastolic flow rates for correcting said systolic and diastolic flow rates transmitted by said main actuator to said driven artificial ventricle and for communicating respectively to the corrected systolic and diastolic flow rates desired values for said driven artificial ventricle.

Thus, with the present invention, the beats of the sealed bag are restricted since, in operation, the hydraulic fluid is transferred from one artificial ventricle to the other. However, with said correction flow rates generated by said auxiliary actuator, the diastole and the systole durations are not necessarily equal.

Besides, the auxiliary actuator can have a lesser power than said main actuator, such that the power consumption of the prosthesis in accordance with this invention is lower than the power consumption of the known prosthesis with two actuators. In addition, the auxiliary actuator can also have a smaller size than the one of said main actuator.

Preferably, the driving artificial ventricle corresponds to the right artificial ventricle, whereas the driven artificial ventricle corresponds to the left artificial ventricle. In addition, it is advantageous that said main and auxiliary actuators are of the volumetric motor pump type.

For the convenience of accommodating the prosthesis inside the pericardial cavity, it is also advantageous that said main actuator and said auxiliary actuator are provided in the vicinity of each other. In this case, in order to benefit from the anatomy, said main and auxiliary actuators are provided in the vicinity of the left artificial ventricle and so they communicate commonly with the hydraulic fluid chamber of this latter ventricle, while said main actuator is connected to the hydraulic fluid chamber of the right artificial ventricle by a duct outside said stiff body.

BRIEF DESCRIPTION OF THE DRAWINGS

The figures of the appended drawing will help better understand how the invention can be implemented. In theses figures, identical references denote similar elements.

FIG. 1 schematically shows in cross-section a known heart prosthesis which the present invention aims at improving.

FIG. 2 schematically illustrates the condition of the heart prosthesis of FIG. 1 at the end of a systole.

FIG. 3 schematically illustrates the condition of the heart prosthesis of FIG. 1 at the end of a diastole.

DETAILED DESCRIPTION OF THE INVENTION

Figure 4:
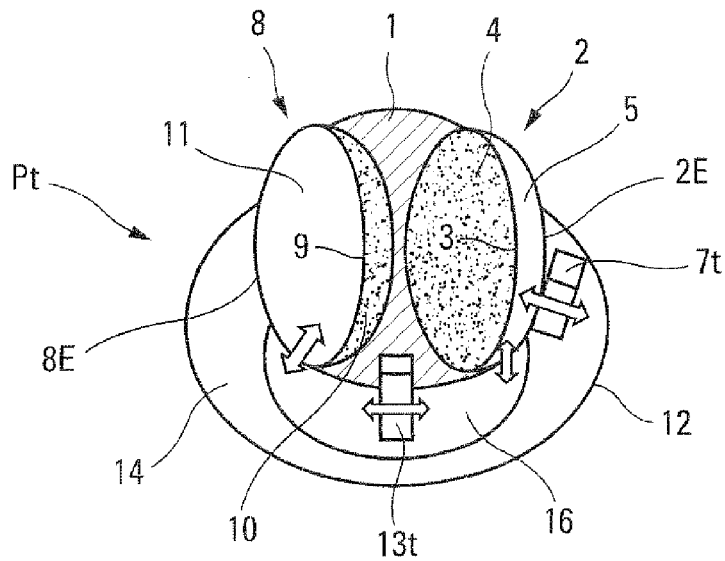
FIG. 4 schematic shows, in a view similar to FIGS. 1 to 3, the heart prosthesis in accordance with this invention.

The known prosthesis P, schematically depicted in FIG. 1, is intended to replace the natural left and right ventricles of an ill heart (not shown), after ablation thereof. The prosthesis P should be able to be accommodated at least substantially in the portion of the pericardial cavity left free following removal of said natural ventricles.

As schematically depicted in FIG. 1, the prosthesis P comprises:
- a stiff body 1 in which an artificial left ventricle 2 is arranged, comprising a soft membrane 3 which sealingly partitions said artificial ventricle 2 into a chamber 4 for the blood flow and a chamber 5 for a hydraulic fluid, said blood chamber 4 being intended to be connected, on one side to the natural left atrium LA in communication with the pulmonary veins PV and, on the other side, to the aorta AO;
- a hydraulic actuator 7, for example of the volumetric motor pump type, in communication with the hydraulic fluid chamber 5 of the artificial left ventricle 2;
- an artificial right ventricle 8, arranged within said stiff body 1 and comprising a soft membrane 9 which sealingly partitions said artificial ventricle 8 into a chamber 10 for the blood flow and a chamber 11 for a hydraulic fluid, said blood chamber 10 being intended to be connected, on one side, to the natural right atrium RA in communication with the vena caves VC and, on the other side, to the pulmonary artery PA; and
- a hydraulic actuator 13, for example also of the volumetric motor pump type, in communication with the hydraulic fluid chamber 11 of the artificial right ventricle 8.

Besides, a soft bag 12 widely and sealingly surrounds at least one portion of the stiff body 1 by enclosing the hydraulic actuators 7 and 13. Such soft bag 12 forms a reservoir 14 for the hydraulic fluid moved by said actuators 7 and 13.

In the pump P, each actuator 7 and 13 is specifically dedicated to one of the artificial ventricles 2 or 8, respectively, such that both actuators 7 and 13 have the same power.

When, as schematically illustrated by FIGS. 2 and 3, actuators 7 and 13 are phase controlled, such that systoles of the artificial ventricles 2 and 8 occur simultaneously (FIG. 2) and diastoles of said artificial ventricles 2 and 8 also occur simultaneously (FIG. 3), the volume of the reservoir 14 made up by the soft bag 12 varies widely. Indeed, in the case of simultaneous systoles (FIG. 2), both hydraulic fluid chambers 5 and 11 are filled with this fluid, such that the reservoir 14 contains little hydraulic fluid and volume thereof is reduced. By contrast, when said artificial ventricles 2 and 8 are in a condition where diastoles thereof are simultaneous (FIG. 3), both hydraulic fluid chambers 5 and 11 empty, such as that reservoir 14 is filled with hydraulic fluid and volume thereof is large.

The prosthesis Pt, according to this invention and depicted in FIGS. 4, 5 and 8 to 11, makes it possible to avoid such a high variation of the volume of the reservoir 14, while requiring a lesser operating power.

Such prosthesis Pt is the same as the prosthesis P described above with respect to elements 1 to 5, 8 to 12 and 14. However:
- the actuator 7 is replaced by an actuator 7t of lower power; and
- the actuator 13 is replaced by an actuator 13t of the same power, but arranged in another way. Indeed, the actuator 13t is not arranged (as the actuator 13) between the hydraulic fluid chamber 11 and the reservoir 14 anymore, but between the hydraulic fluid chambers 5 and 11 of both artificial ventricles 2 and 8.

Thus, said actuator 7t is of lesser power and can be less cumbersome than said actuator 13t.

Figure 5:
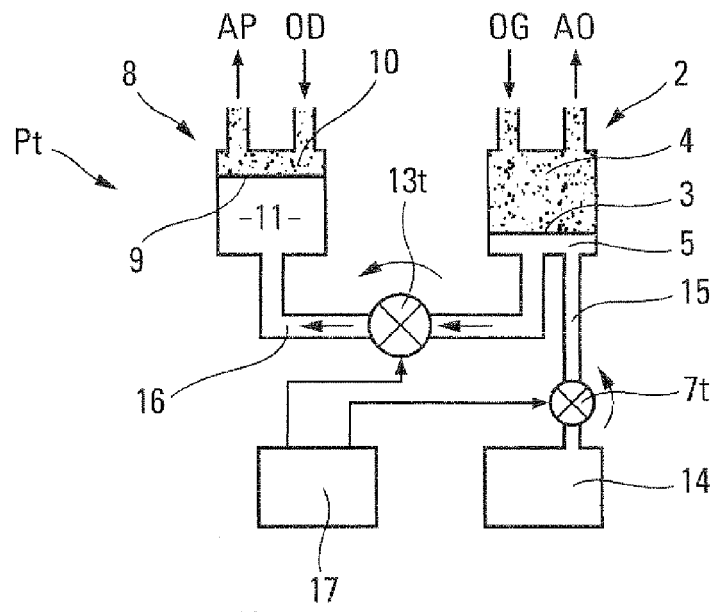
FIG. 5 is the block diagram of the heart prosthesis of FIG. 4.

The block diagram of the prosthesis Pt, shown in FIG. 5 and wherein the artificial ventricles 2 and 8 are depicted as cylinders in which pistons made up of the membranes 3 and 9 move respectively, helps better understand the operation of the prosthesis Pt of FIG. 4. It can be seen that the actuator 7t is provided in a link 15 connecting the reservoir 14 and the fluid chamber 5 of the artificial ventricle 2 and that the actuator 13t is provided in a link 16 connecting both fluid chambers 5 and 11 of the artificial ventricles 2 and 8.

A device 17 controls the operation of actuators 7t and 13t, such that the actuator 13t plays a leading role, whereas the actuator 7t plays a secondary role in correcting the flow rate.

Figure 6:
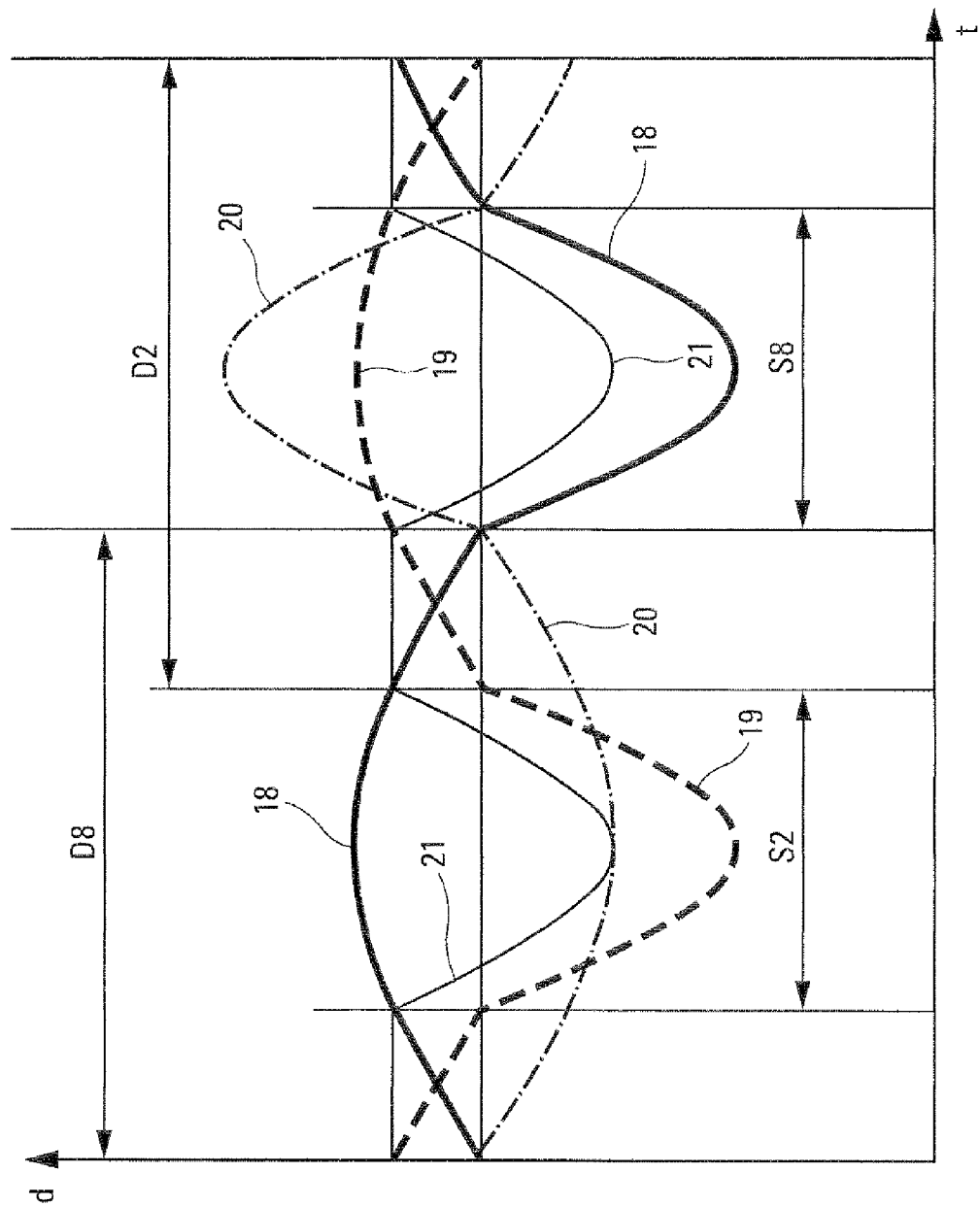
FIG. 6 illustrates the operation of the heart prosthesis of FIGS. 4 and 5 for normal diastolic and systolic flow rates.

The operation of the prosthesis Pt is explained in further detail thereafter with respect to the time chart of FIG. 6. In this time chart, different hydraulic fluid flow rates d are shown (corresponding to blood rates respectively) as a function of time t. There is particularly shown (in full line) a curve 18 corresponding to flow rates of desired values for the main actuator 13t during diastoles D8 and systoles S8 of the artificial ventricle 8, as well as (in dash lines) a curve 19 corresponding to flow rates with desired values for the auxiliary actuator 7t during diastoles D2 and systoles S2 of the artificial ventricle 2. It will be noticed that, in the example shown, the systoles S2 and S8 have lower durations than the diastoles D2 and D8.

The device 17 controls the main actuator 13t such that it transmits to the artificial ventricle 8 the desired diastolic and systolic flow rates, represented by curve 18. The artificial ventricle 8 therefore supplies the desired blood volumes.

However, because of the existing link 16 between the hydraulic fluid chambers 5 and 11 of the artificial ventricles 2 and 8, the main actuator 13t imposes to the artificial ventricle 2 systolic and diastolic flow rates represented by curve 20 in chain dotted lines, such that the systolic and diastolic flow rates of said artificial ventricle 2 are respectively the opposites of diastolic and systolic flow rates of the artificial ventricle 8 (curve 18). In such operation, the artificial ventricle 8 is therefore a driving one whereas the artificial ventricle 2 is a driven one.

Also, in order that the artificial ventricle 2 can receive the desired flow rates represented by curve 19, the device 17 controls the auxiliary actuator 7t such that it transmits to said artificial ventricle 2, correction systolic and diastolic flow rates (represented by curve 21 in FIG. 6) capable of correcting said systolic and diastolic flow rates (curve 20) imposed by the main actuator 13t.

Figure 7:
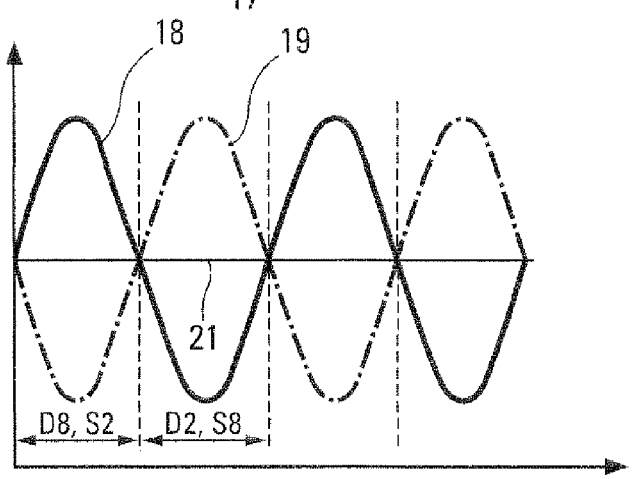
FIG. 7 illustrates the operation of the heart prosthesis of FIGS. 4 and 5 for high diastolic and systolic flow rates.

FIG. 6 shows diastolic and systolic flow rate forms corresponding to average normal blood flow rates, for example in the order of 5 liters per minute. In the case where the blood flow rate is high, for example in the order of 8 liters by minute, the flow rate forms would rather be as depicted in FIG. 7. In this case, the curves 18 and 19 would look like identical sinusoids in phase opposition, such that therefore, no correction would be required from the auxiliary actuator 7t (which is depicted in FIG. 7 because curve 21 merges with axis of the sinusoids 18 and 19).

Figure 9:
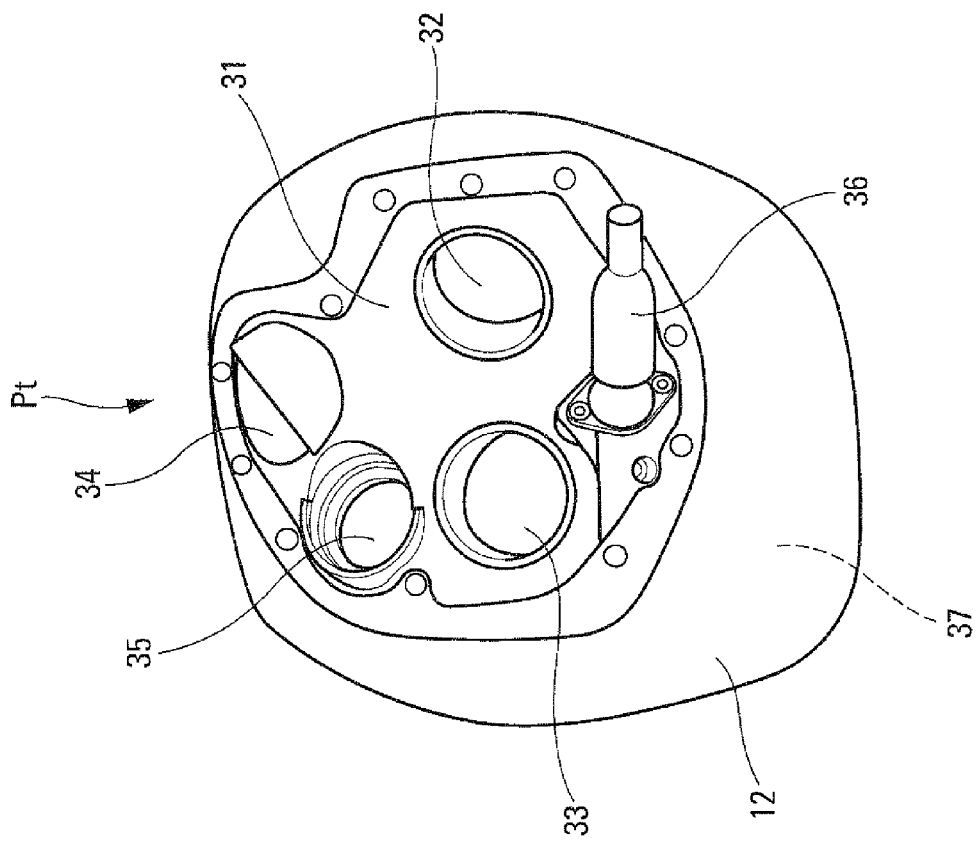
FIG. 9 is a top view of the prosthesis of FIG. 8.
Figure 8:
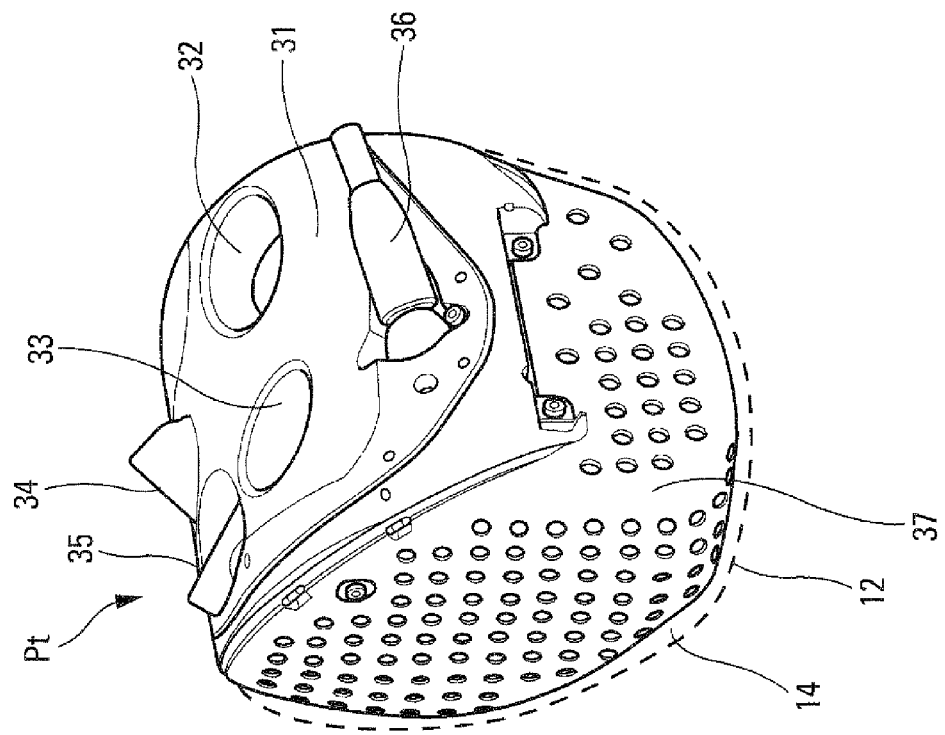
FIG. 8 is a perspective view of a practical embodiment of the prosthesis of the invention, wherein its envelope made of a sealed soft bag is assumed to be transparent.

In the practical embodiment depicted in FIGS. 8 and 9, the prosthesis Pt is in the form of an anatomical shape volume (corresponding to that of the pericardial cavity) comprising a plate 31 on which a connecting port 32 for the natural left atrium LA, a connecting port 33 for the natural right atrium RA, a connecting port 34 for the aorta AO and a connecting port 35 for the pulmonary artery PA, are bored. In addition, on these figures, the base 36 of an electrical connection with the outside of said prosthesis Pt is depicted.

The heart prosthesis is sealingly enclosed within the soft bag 12 (assumed to be clear in FIG. 8) surrounding said prosthesis, in a wide fashion, and filled with hydraulic fluid actuated by the actuators 7t and 13t, immersed in this fluid. The soft bag 12 provides the reservoir 14 acting as a tarpaulin for this hydraulic fluid.

The body 1 and the actuators 7t and 13t are wrapped in a stiff cut-out wall 37, serving as a strainer and enabling hydraulic fluid flow inside the bag 12. The cut-out wall 37 prevents said soft bag from being suctioned by actuators 7t and 13t.

Figure 10:
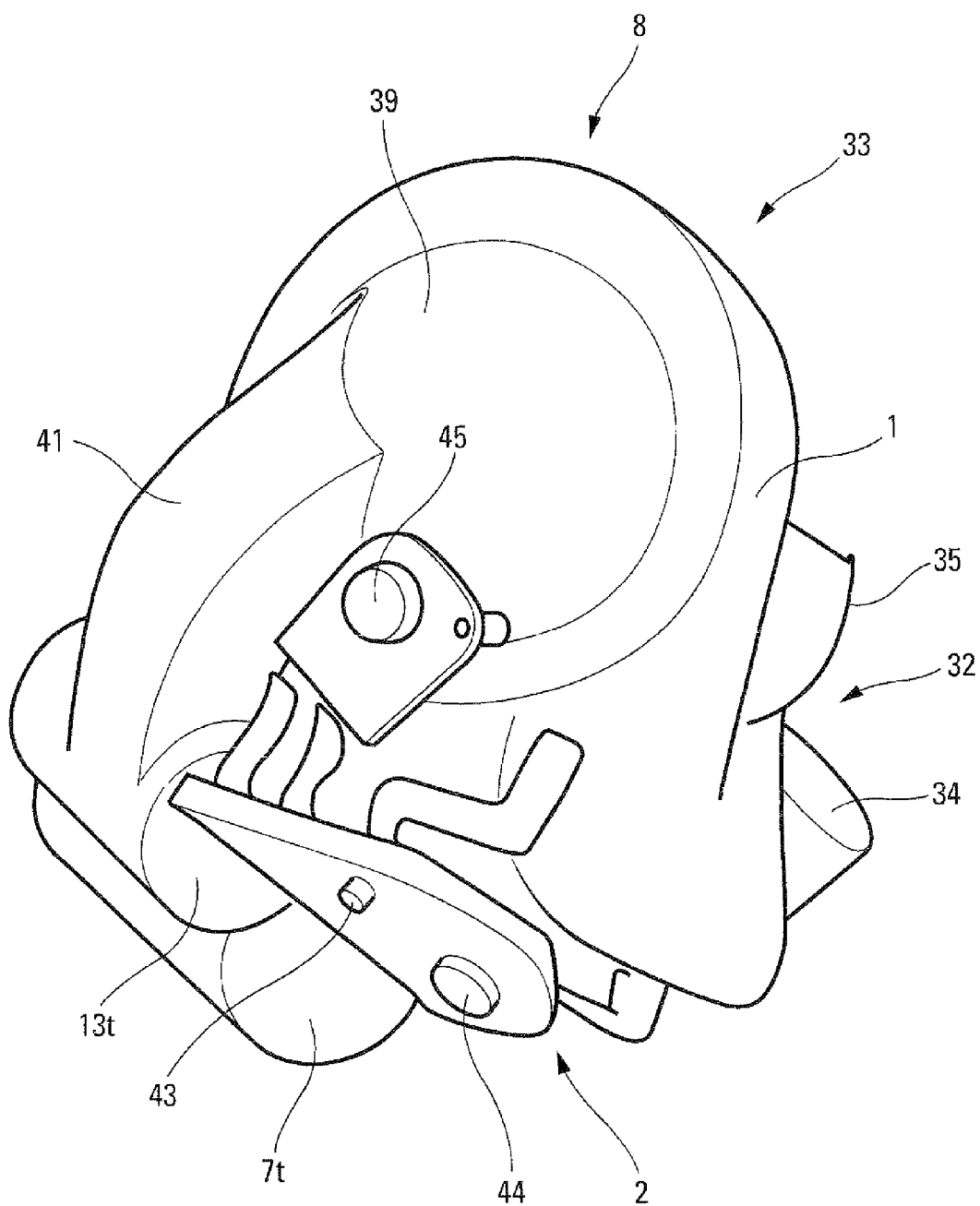
FIG. 10 is a perspective view of the prosthesis of FIGS. 8 and 9, after removal of said sealed soft bag and the enveloping cut-out wall.

On FIG. 10, an embodiment of the body 1 and actuators 7t and 13t as a whole located inside the cut-out wrapping wall 37 and soft bag 12 is depicted in perspective. In this figure, it can be seen that the auxiliary and main actuators 7t and 13t have been provided close to each other, in the vicinity of the artificial left ventricle 2. In addition, as shown more clearly in FIG. 11, the outside walls 2E and 8E of the hydraulic fluid chambers 5 and 11 of the artificial ventricles 2 and 8 (see also FIG. 4) are formed by removable covers 38 and 39 intended to seal said ventricles, respectively.

The auxiliary actuator 7t communicates with the chamber 5 of the artificial left ventricle 2 through a port 40 going through the cover 38 and acting as the link 15 of FIG. 5. The main actuator 13t communicates, on the one hand, with the chamber 5 of the artificial ventricle 2 through the same port 40 and, on the other hand, with the chamber 11 of the artificial ventricle 8 through an outside duct 41 opening to a port 42 in the cover 39. The duct 41 and the ports 40 and 42 correspond to the link 16 of FIG. 5.

Figure 11:
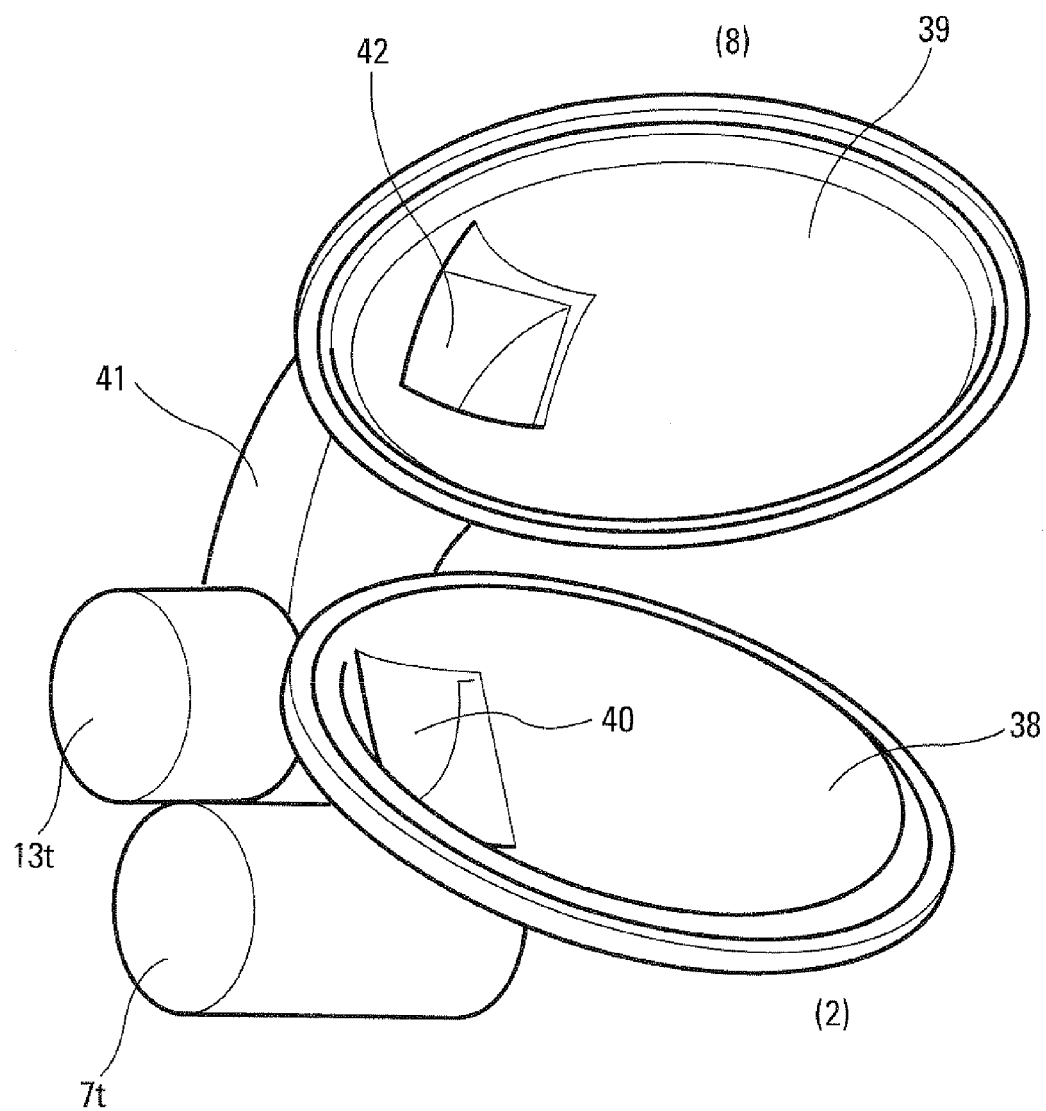
FIG. 11 is a perspective view showing hydraulic actuators and covers of artificial ventricles of the prosthesis of FIGS. 8 to 10.

As depicted in FIG. 11, the actuators 7t and 13t, the covers 38 and 39 and the duct 41 can be integral with one another to form a construction unit.

In FIG. 10, electronic driving elements are further depicted, such as a sensor 43 for the pressure inside the soft bag 12, a sensor 44 for the pressure in the left artificial ventricle 2 and a sensor 45 for the pressure in the right artificial ventricle 8.

The invention claimed is:

1. A cardiac prosthesis implantable in the pericardial cavity of a patient, said prosthesis for replacing the patient's natural left and right ventricles after ablation thereof and comprising:
   a stiff body having an artificial left ventricle and an artificial right ventricle,
   wherein one of the artificial left ventricle and the artificial right ventricle is a driven artificial ventricle and the other is a driving artificial ventricle, and each artificial ventricle comprises a cavity that is sealingly partitioned by a soft pulsatile membrane into a blood flow chamber and a hydraulic fluid chamber, with the blood flow chamber of the artificial left ventricle being configured to connect to the patient's natural left atrium and to the patient's aorta, and the blood flow chamber of the artificial right ventricle being configured to connect to the patient's natural right atrium and to the patient's pulmonary artery;
   two hydraulic actuators connected to the hydraulic fluid chambers of said artificial ventricles, with the hydraulic actuators being configured to alternately inject and expulse hydraulic fluid from each hydraulic fluid chamber at desired values of diastolic and systolic flow rates; and
   a soft bag sealingly surrounding at least one portion of said stiff body and enclosing said hydraulic actuators, said soft bag configured as a hydraulic fluid reservoir for each of said hydraulic actuators and as a compliance chamber,
   wherein:
   one of said actuators is configured as a main actuator in fluid connection between the hydraulic fluid chamber of the driven artificial ventricle and the hydraulic fluid chamber of the driving artificial ventricle,
   the other of said actuators is configured as an auxiliary actuator in fluid connection one and is provided between the hydraulic fluid chamber of said driven artificial ventricle and said hydraulic fluid reservoir, and;
   the main actuator is configured to:
     transmit to said driving artificial ventricle diastolic and systolic flow rates having desired respective values for the this driving artificial ventricle, and
     transmit to said driven artificial ventricle:
       a systolic flow rate opposite to said diastolic flow rate of a desired value for said driving artificial ventricle, and
       a diastolic flow rate opposite to said systolic flow rate of a desired value for said driving artificial ventricle; and
   the auxiliary actuator is configured to transmit to said driven artificial ventricle correction systolic and diastolic flow rates that correct said systolic and diastolic flow rates transmitted by said main actuator to said driven artificial ventricle and communicate the corrected systolic and diastolic flow rates as desired values for said driven artificial ventricle.

2. The cardiac prosthesis according to claim 1, wherein said auxiliary actuator has a lesser is lower in power relative to said main actuator.

3. The cardiac prosthesis according to claim 2, wherein said auxiliary actuator is smaller in size relative to said main actuator.

4. The cardiac prosthesis according to claim 1, wherein the driving artificial ventricle corresponds to the right artificial ventricle, and the driven artificial ventricle corresponds to the left artificial ventricle.

5. The cardiac prosthesis according to claim 1, wherein said main actuator are of the volumetric motor pump type.

6. The cardiac prosthesis according to claim 1, wherein said main actuator and said auxiliary actuator are provided in proximity to one another.

7. The cardiac prosthesis according to claim 2, wherein said main and auxiliary actuators are provided in proximity to the left artificial ventricle and communicate commonly through a port with the hydraulic fluid chamber of said left artificial ventricle, and said main actuator is connected to the hydraulic fluid chamber of said right artificial ventricle through a duct outside said stiff body.

* * * * *